US008486043B2

(12) United States Patent
Iyer et al.

(10) Patent No.: US 8,486,043 B2
(45) Date of Patent: Jul. 16, 2013

(54) INHALATION DRUG DELIVERY

(75) Inventors: Laxmi Iyer, Milpitas, CA (US); Paul S. Uster, Pleasanton, CA (US)

(73) Assignee: MAP Pharmaceuticals, Inc., Mountain View, CA (US)

( * ) Notice: Subject to any disclaimer, the term of this patent is extended or adjusted under 35 U.S.C. 154(b) by 878 days.

(21) Appl. No.: 12/250,516

(22) Filed: Oct. 13, 2008

(65) Prior Publication Data
US 2009/0157037 A1 Jun. 18, 2009

Related U.S. Application Data

(60) Provisional application No. 60/979,791, filed on Oct. 12, 2007.

(51) Int. Cl.
| | |
|---|---|
| *A61B 19/00* | (2006.01) |
| *A61M 5/31* | (2006.01) |
| *A61M 37/00* | (2006.01) |
| *A61M 16/00* | (2006.01) |
| *A61K 9/14* | (2006.01) |
| *A61K 9/50* | (2006.01) |
| *A62B 7/00* | (2006.01) |
| *B05D 7/14* | (2006.01) |
| *B65D 35/22* | (2006.01) |
| *B65D 51/16* | (2006.01) |

(52) U.S. Cl.
USPC ............. 604/403; 604/87; 604/240; 604/241; 604/244; 424/489; 424/499; 424/502; 128/200.24; 128/203.14; 128/203.15; 215/32; 215/249; 215/251; 215/256; 215/311; 215/DIG. 3; D24/164; D24/224; 222/94; 222/107; 222/541

(58) Field of Classification Search
USPC .... 424/489, 499, 502; D24/164, 224; 222/94, 222/107, 541; 215/32, 249, 251, 256, 311, 215/DIG. 3; 128/200.24, 203.14, 203.15; 604/87, 240, 241, 244
See application file for complete search history.

(56) References Cited

U.S. PATENT DOCUMENTS 4,477,452 A * 10/1984 Haeger .......................... 514/196
5,145,684 A 9/1992 Liversidge et al.
5,346,702 A 9/1994 Na et al.
6,264,922 B1 7/2001 Wood et al.
6,267,989 B1 7/2001 Liversidge et al.

(Continued)

FOREIGN PATENT DOCUMENTS

EP 0 388 360 A2 9/1990
WO WO03/086268 * 10/2003

(Continued)

OTHER PUBLICATIONS

International Search Report mailed Dec. 12, 2008, for PCT Application PCT/US2008/079754 filed Oct. 13, 2008, eight pages.

(Continued)

*Primary Examiner* — Jane C Oswecki
(74) *Attorney, Agent, or Firm* — Jennifer C. Cheng

(57) ABSTRACT

Described here are unit dose containers, methods, and kits for treating asthma and other pulmonary conditions by nebulization. The unit doses of active agents are provided in a low volume formulation, which results in faster nebulization of the unit doses. The containers are also formed to minimize internal surface area so that effective re-dispersion of the active agents can be achieved while reducing adsorption to the walls of the containers.

26 Claims, 7 Drawing Sheets

U.S. PATENT DOCUMENTS

Figure 1:
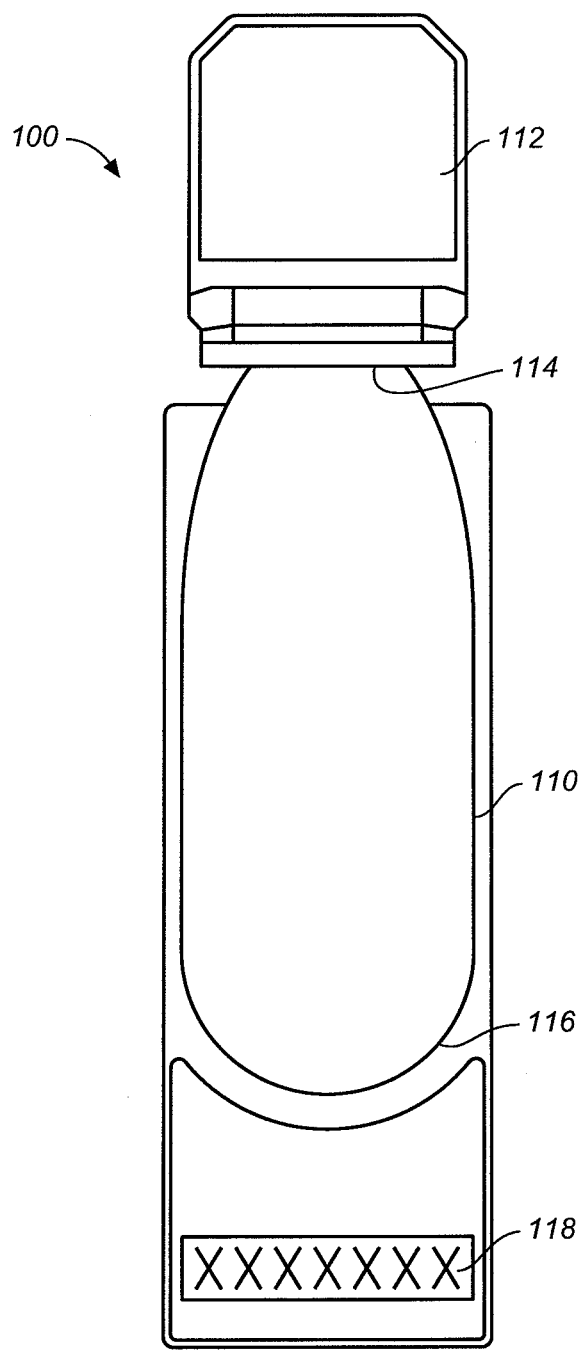

| | | |
|---|---|---|
| 6,792,939 B1 | 9/2004 | Weinstein |
| 6,811,767 B1 | 11/2004 | Bosch et al. |
| 2003/0091513 A1 | 5/2003 | Mohsen et al. |
| 2004/0109826 A1* | 6/2004 | Malladi et al. .................. 424/45 |
| 2007/0172347 A1 | 7/2007 | Battig et al. |
| 2007/0178051 A1* | 8/2007 | Pruitt et al. ..................... 424/46 |
| 2009/0081297 A1 | 3/2009 | Cook et al. |

FOREIGN PATENT DOCUMENTS

| | | | |
|---|---|---|---|
| WO | WO-03/086268 A1 | | 10/2003 |
| WO | WO2005/122719 | * | 12/2005 |
| WO | WO-2005/122719 A2 | | 12/2005 |
| WO | WO-2005/122719 A3 | | 12/2005 |
| WO | WO2007/003891 | * | 1/2007 |
| WO | WO-2007/003891 A1 | | 1/2007 |

OTHER PUBLICATIONS

U.S. Appl. No. 11/409,922, filed Apr. 24, 2006, by Cook et al.

Written Opinion mailed Dec. 12, 2008, for PCT Application No. PCT/US2008/079754 filed Oct. 13, 2008, 6 pages.

* cited by examiner

INHALATION DRUG DELIVERY

CROSS-REFERENCE TO RELATED APPLICATIONS

This application claims priority to U.S. Provisional Patent Application Ser. No. 60/979,791, filed Oct. 12, 2007, which is herein incorporated by reference in its entirety.

FIELD

The containers and kits described here are in the field of aerosol drug delivery. Specifically, unit dose containers designed to hold low volumes of formulations and minimize adsorption and agglomeration of particulate active agents contained therein are described. Methods for administering active agents using the unit dose containers to treat various allergic and inflammatory conditions, and various pulmonary conditions are also described.

BACKGROUND

Asthma is a pulmonary condition characterized by airway inflammation, airway hyperresponsiveness, and reversible airway obstruction. During asthmatic episodes, afflicted individuals often experience labored breathing, wheezing, and coughing. Of the estimated 20 million asthma patients in the United States, there are about six million children under 18 years of age and over one million children under five years of age with asthma (National Health Interview Survey, 2004). Asthma in children has increased dramatically in both numbers and severity over the last 15 years.

Nearly all pediatric asthma patients require nebulizers for administration of steroid therapy. This is due to either a lack of the breath coordination needed for pressurized metered-dose inhalers (pMDIs) or a lack of the lung capacity needed to use dry powder inhalers (DPIs). Formulations that undergo nebulization are dispersed in air to form an aerosol of very fine liquid droplets suitable for inhalation into the lung. Nebulizers typically use compressed air, piezoelectric or servomechanically generated ultrasonic waves, or a vibrating mesh to create the mist of the droplets, and may also have a baffle to remove larger droplets from the mist by impaction. A variety of nebulizers are available for this purpose, such as soft mist nebulizers, vibrating mesh nebulizers, ultrasonic nebulizers, jet nebulizers, and breath-actuated nebulizers. Examples of commercially available nebulizers include the AERONEB™ and AERONEB GO™ nebulizers (Aerogen, San Francisco, Calif.); PARI nebulizers, including the PARI LC PLUS™, PARI BOY™ N, PARI eflow, PARI LC SINUS, PARI SINUSTAR™, PARI SINUNEB, and PARI DURANEB™ nebulizers (PARI Respiratory Equipment, Inc., Monterey, Calif.); MICROAIR™ nebulizer (Omron Healthcare, Inc, Vernon Hills, Ill.); HALOLITE™ nebulizer (Profile Therapeutics Inc., Boston, Mass.); RESPIMAT™ nebulizer (Boehringer Ingelheim Ingelheim, Germany); ERODOSE™ nebulizer (Aerogen, Inc., Mountain View, Calif.); OMRON ELITE™ (Omron Healthcare, Inc., Vernon Hills, Ill.); OMRON MICROAIR™ (Omron Healthcare, Inc, Vernon Hills, Ill.); MABISMIST™ II nebulizer (Mabis Healthcare, Inc, Lake Forest, Ill.); LUMISCOPE™ 6610 nebulizer; (The Lumiscope Company, Inc., East Brunswick, N.J.); AIRSEP MYSTIQUE™ nebulizer, (AirSep Corporation, Buffalo, N.Y.); ACORN-1 and ACORN-11 (Vital Signs, Inc, Totowa, N.J.); AQUATOWER™ nebulizer (Medical Industries America, Adel, IA); AVA-NEB (Hudson Respiratory Care Incorporated, Temecula, Calif.); AEROCURRENT™ nebulizer utilizing the AEROCELL™ disposable cartridge (AerovectRx Corporation, Atlanta, Ga.); CIRRUS (Intersurgical Incorporated, Liverpool, N.Y.); DART (Professional Medical Products, Greenwood, S.C.); DEVILBISS™ PULMO AIDE (DeVilbiss Corp; Somerset, Pa.); DOWNDRAFT™ (Marquest, Englewood, Colo.); FAN JET (Marquest, Englewood, Colo.); MB-5 (Mefar, Bovezzo, Italy); MISTY NEB™ (Baxter, Valencia, Calif.); SALTER 8900 (Salter Labs, Arvin, Calif.); SIDESTREAM™ (Medic-Aid, Sussex, UK); UPDRAFT-II™ (Hudson Respiratory Care; Temecula, Calif.); WHISPER JET™ (Marquest Medical Products, Englewood, Colo.); AIOLOS™ (Aiolos Medicnnsk Teknik, Karlstad, Sweden); INSPIRON™ (Intertech Resources, Inc., Bannockburn, Ill.); OPTIMIST™ (Unomedical Inc., McAllen, Tex.); PRODOMO™ and SPIRA™ (Respiratory Care Center, Hameenlinna, Finland); AERx™, Essence™, and Ultra™ nebulizers (Aradigm Corporation, Hayward, Calif.); SONIK™ LDI Nebulizer (Evit Labs, Sacramento, Calif.); and SWIRLER® Radioaerosol System (AMICI, Inc., Spring City, Pa.). Exemplary vibrating membrane, mesh or plate nebulizers are described by R. Dhand (Respiratory Care, (December 2002), 47(12), p. 1406-1418). In use, the nebulized formulation is administered to the individual via a mouthpiece or mask. Presently, Pulmicort Respules® ampules (Astrazeneca, Wilmington, Del.) are the only FDA approved nebulized steroid product on the market for the treatment of pediatric asthma.

Low patient compliance is a generally known problem with nebulized drugs. This is primarily due to the amount of time required for nebulizing the drug, which can last up to 30 minutes or longer, depending on such factors as the volume of liquid formulation to be nebulized, the particular active agent being nebulized, the concentration and surface tension of the active agent in the formulation, and the resulting viscosity of the formulation. Other factors include the condition or symptom being treated, and whether the active agent is present as a solution or suspension. Active agent formulations are generally supplied as nominal 2.0 ml volumes with solution or suspension viscosities ranging from that of water, to 100 times the viscosity of water. These typically require about four to about 30 minutes to nebulize, with the nebulization time increasing as the viscosity increases from that of water. If the formulation is a suspension, an additional 15% to 30% longer time is required to nebulize than solution formulations with comparable viscosities due to the added energy required to from droplets containing suspended particulates. Children and adults who become impatient because of lengthy nebulization times often stop treatment prematurely. This can lead to further non-compliance since the inadequate dose will likely fail to provide adequate therapy, and thus discourage further use of the nebulizer treatment regimen.

Another issue with currently available nebulizer ampules relates to settling of the drug during their extended storage. Thus, prior to use, the ampules are shaken to re-disperse the drug within the formulation. In addition to most ampules lacking sufficient headspace to easily facilitate re-dispersion upon shaking, shaking can lead to unwanted drug adherence to the interior surface of the ampules.

Consequently, new containers, kits, and methods for delivering one or more unit doses of an active agent via nebulization for treating asthma and other pulmonary conditions, as well as allergic and inflammatory conditions would be useful. Specifically, containers capable of improving formulation stability would be desirable. Containers that provide more efficient delivery of formulations would also be desirable.

SUMMARY

The unit dose containers, kits, and methods described here provide efficient delivery of active agents to the lungs to treat asthma and other pulmonary conditions, allergic conditions, and inflammatory conditions. The containers are also configured to provide enhanced storage stability of the formulations contained therein. The containers described here deliver active agents with shorter nebulization times than conventional nebulizer ampules. In some instances, the active agents are delivered in half the time or less than is required for conventional nebulizer ampules. The containers also provide storage conditions that reduce particle agglomeration and surface adsorption. In some variations, there is less than 20% surface adsorption of the active agent after re-dispersion. In other variations, there is less than 15% surface adsorption of the active agent after re-dispersion. In yet further variations, there is less than 10% surface adsorption of the active agent after re-dispersion. Accordingly, there is better recovery of active agents after extended storage when the containers are used. To reiterate, there is no substantial agglomeration or surface adsorption of active agents when formulations are stored in the containers described here. As used herein, the phrases "no substantial agglomeration" or "minimal agglomeration" refer to an increase in particle size of not more than about 150 nm over a 12 month storage period.

The containers generally include a body for holding lower volumes of the active agent formulation, a dispensing end, which is the opening that allows the formulation to exit the container, a distal end, and a cap for removably sealing the dispensing end. As further described below, the cap may be configured as a frangible tab that separates from the dispensing end when a twisting motion is applied to the tab. The containers are designed to hold between about 50 μl to about 2.0 ml of the formulation.

In general, lowering or decreasing the nebulization volume will shorten the nebulization time proportionally at the same concentrations or viscosity of the formulation. The cavity usually has a lower wetted (internal) surface area (in comparison to commercially available nebulizer containers) to minimize the amount of surface absorption of the active agent to exposed areas of the internal surface of the container wall. The containers are also designed with a wider or larger dispensing end. This creates sufficient headspace above the formulation so that re-dispersion of the active agent prior to nebulization can be effectively achieved, and allows more complete dispensing of the filled volume when the nebule is inverted and squeezed.

The nebulized active agent is generally used to treat asthma and other pulmonary conditions, allergic conditions, and inflammatory conditions. In particular, asthma in the pediatric patient population is treated. Containers such as vials, ampules, canisters, and the like, are designed to hold a unit dose of the active agent. In one variation, budesonide is the active agent included in the containers to treat pediatric asthma. The unit dose containers may also be provided as kits. The kits may be formed by packaging together a plurality of individual unit dose containers or a plurality of sleeves of containers.

BRIEF DESCRIPTION OF THE DRAWINGS

FIG. 1 is a front view of an exemplary unit dose container.

FIG. 2 is a front view of a unit dose container without the cap to better show the dispensing end of the container.

FIG. 3 is a top view of the dispensing end and cap shown in FIG. 1.

FIG. 4 is a side view of the unit dose container shown in FIG. 1. A partial cutout of the container is also shown to depict wall thickness.

FIG. 5 is a front view of an exemplary sleeve of vials.

FIG. 6 provides additional drawings of the unit dose containers and components shown in FIGS. 1-5.

FIG. 7 is a graph comparing re-dispersion of budesonide in exemplary unit dose containers subjected to moderate shaking at label claims of 0.0714 mg/ml, 0.1213 mg/1.5 ml, and 0.2252 mg/ml.

FIG. 8 is a graph comparing re-dispersion of budesonide in exemplary unit dose containers subjected to severe shaking at label claims of 0.0714 mg/ml, 0.1213 mg/1.5 ml, and 0.2252 mg/ml.

DETAILED DESCRIPTION

The unit dose containers, kits, and methods described here provide efficient delivery of active agents to the lungs to treat asthma and other pulmonary conditions, allergic conditions, and inflammatory conditions. The containers are also configured to provide enhanced storage stability of the formulations contained therein. In general, the containers comprise a unit dose amount of an active agent, which is typically delivered faster than unit doses from commercially available nebulizer ampules to the airways of the pulmonary system. This is because the containers include lower volumes of formulation than conventional ampules.

In addition to asthma, the pulmonary conditions may be selected from the group consisting of, without limitation, chronic obstructive pulmonary disease (COPD), including emphysema; cystic fibrosis; respiratory tract infections such as laryngitis, tracheitis, bronchitis, bronchiolitis, and pneumonia; neoplasms of the large and small airways; nasopharynx tumors; respiratory distress syndrome; and allergic or inflammatory conditions affecting the eyes, ears, or nose. As used herein, the terms "treat" or "treating" refer to the resolution of a pulmonary condition or the prevention or amelioration of a sign or symptom of a pulmonary condition, including signs or symptoms that are considered sequelae of the condition. Furthermore, as used herein, the term "container" refers to any vessel, e.g., a vial, ampule, canister, etc., that is capable of holding a unit dose of an active agent for nebulization.

I. CONTAINERS

Container Design. The containers may be of any dimension so long as they hold a low volume of a formulation for nebulization and have a low internal surface area. Conventional unit dose containers have wetted surface areas greater than approximately 3.0 square inches (19.7 square centimeters). The containers described here generally have wetted surface areas of less than about 3.0 square inches (19.7 square centimeters), less than about 2.5 square inches (16.1 square centimeters), less than about 2.0 square inches (12.0 square centimeters), and in some instances, less than about 1.5 square inches (9.7 square centimeters). In some variations, the containers have a wetted surface area of about 1.5 square inches (9.7 square centimeters). In other variations, the containers have a wetted surface area of less than about 1.0 square inch (6.44 square centimeters), less than about 0.50 square inches (3.22 square centimeters), or less than about 0.25 square inches (1.61 square centimeters).

Conventional unit dose containers also have filled liquid volumes of approximately 1.9 ml or greater. The containers herein described typically have filled liquid volumes of about 2.0 ml or less, and in some instances, about 1.6 ml or about 1.5 ml or less. Exemplary container designs are shown in FIGS. 1-6. Given that the containers described here include lower formulation volumes, nebulization times of the formulation may generally be about 10%, about 20%, about 30%, about 40%, or about 50% or more faster than with conventional containers (see Example 3). The containers may be between about 3.5 cm to about 5.0 cm in length. The containers may also be designed for single use, or unit use, and provide a unit dose of an active agent to the respiratory tract upon nebulization. In some variations, the containers hold a unit dose of a combination of active agents.

According to one variation, as shown in FIG.1, container 100 includes a body 110 and a cap 112. The body 110 has a dispensing end 114, a distal end 116, and a hollow cavity within the body 110 for holding the formulation for nebulization. The hollow cavity has a cavity wall. The cap 112 is removably attached to dispensing end 114 and reversibly seals the dispending end 114. In some variations the attachment between the cap (tab) 112 and dispensing end 114 may be frangible. For example, the thickness of the material between the cap 112 and dispensing end 114 may be less so that application of a force to either or both of the cap 112 and dispensing end 114 will separate them from one another. In another variation, the cap 112 may be coupled to the dispensing end 114 using an adhesive that allows separation of the cap from the dispensing end when a force is applied to either or both components. Given that the cavity is in fluid communication with dispensing end 114, removal of cap 112, e.g., by a twisting motion, allows the formulation within the container to be poured, squeezed, or otherwise placed into the appropriate portion of the nebulizer.

The distal end 116 has a rounded or curved geometry instead of sharp corners. Varying degrees of roundness or curvature may be employed so long as the resultant geometry minimizes the internal surface area of the container to about 9.7 square centimeters or less, and leaves sufficient headspace in the container to allow effective re-dispersion of the active agent prior to use. The distal end is generally designed with a smooth, spherical convergence to minimize voids or cavities where the active agent can collect and be retained. The cavity typically follows the same outline of the body 110, but may have a different contour if desired, to facilitate re-dispersion of the active agent or reduce internal surface area or volume of formulation to be held in the container. In some variations, the cavity has a size, shape, contour, etc., that results in less than 10% of the active agent (i.e., filled active agent) being adsorbed to the cavity wall after re-dispersion of the active agent. An identifier 118, such as a printed or imprinted label or barcode, etc., may be optionally placed near the distal end 116 for providing information such as type and expiration date of the active agent, compatible nebulizers, and/or lot or batch numbers. Although shown near the distal end 16 in FIG. 1, placement of identifier 118 is not so limited, and may be placed on or attached to any part of the container 100.

Figure 2:
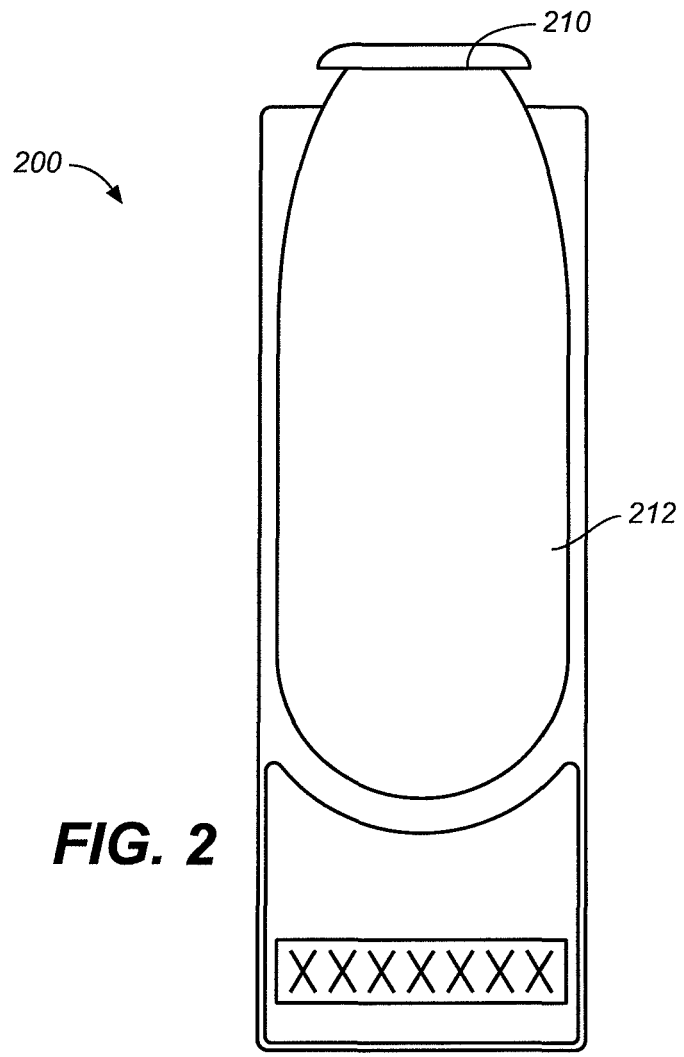
Figure 3:
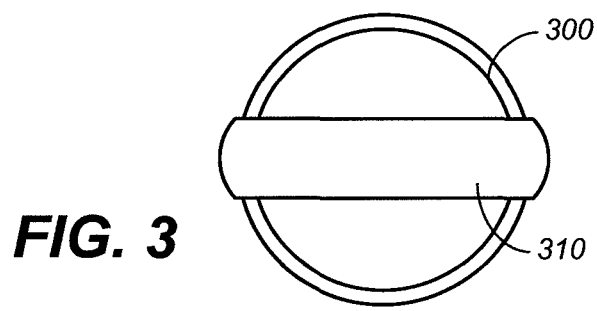

The containers may be fashioned with a dispensing end that is shaped to be larger than the dispensing ends of conventional unit dose containers so that there is a necking region, or alternatively, no appreciable neck region is formed. The lack of a neck region prevents active agent from adhering to the surface of that portion and consequently, becoming absorbed, adsorbed, or chemically degraded in the air or gas-rich headspace. For example, the dispensing end may be formed with a width or diameter that is slightly less than the width or diameter of the body portion of the container. The width or diameter of the dispensing end may be from between about 1.0 cm to about 1.5 cm, or even between about 0.5 cm to about 1.5 cm, but the containers described here may have dispensing ends of any dimension, so long as they do not create a neck region in which an undesirable amount of active agent could become trapped. In the instance where the container is designed to include a neck region, the neck will be configured to have a smaller diameter than the diameter of the cavity. Further, the convergence between the neck and cavity will be designed to be smooth and continuous to avoid creating spaces that can potentially retain active agent or fluid, and to minimize headspace and surface area, but allow sufficient volume to enable fluid agitation when shaken. FIG. 2 shows an exemplary container 200 having a wide dispensing end 210 that does not form a neck region with the container body portion 212. FIG. 3 is illustrative of the dispensing end shown in FIG. 1. In FIG. 3, dispensing end 300 has a circular geometry and diameter that approximates the length of cap 310. Dispensing end 300 may also be formed to be elliptical, or polygonal, but any cross-sectional shape may be employed so long it is continuous with large radii at the vertices to thus avoid sharp vertices which can retain fluid or active agent.

Figure 4:
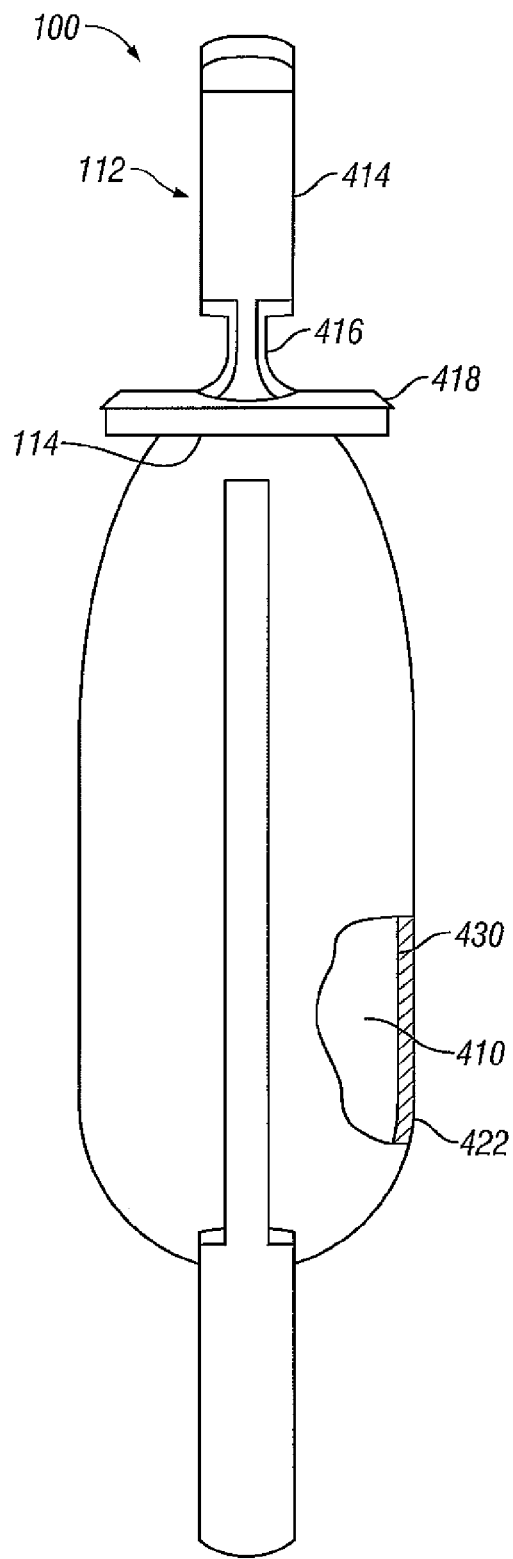

FIG. 4 is a side view of the container shown in FIG. 1. In FIG. 4, cap 112 is removably attached to dispensing end 114, and has a flat grasping portion 414, a stem region 416, and a sealing surface 418 that removably seals the dispensing end 114 to thereby keep the formulation within the container 100. Flat grasping portion 414 is typically at least about 1.0 cm in width and height. the cap 112 may be detached from the dispensing end 114 by holding grasping portion 414 between the fingers and twisting cap 112. Specifically, the twisting motion creates a shearing force which separates the sealing surface 418 from the dispensing end 114. The grasping portion, stem region, and sealing surface may be variously configured to provide a more effective seal and/or cap that is more easily separated from the container, which has a hollow cavity 410 within the body for holding the formulation for nebulization. The wall 422 of the container 100, which has an internal surface 430, is also configured to allow discharge of the formulation when the container 100 is squeezed. The container may be emptied more efficiently than conventional ampules. As shown in Example 7, the residual volume of the instant containers was at least five times lower than that of conventional ampules after one squeeze. Wall thickness may range from between about 0.4 mm to about 0.7 mm, but any wall thickness may be used, so long as it easily allows the container to be squeezed.

Figure 5:
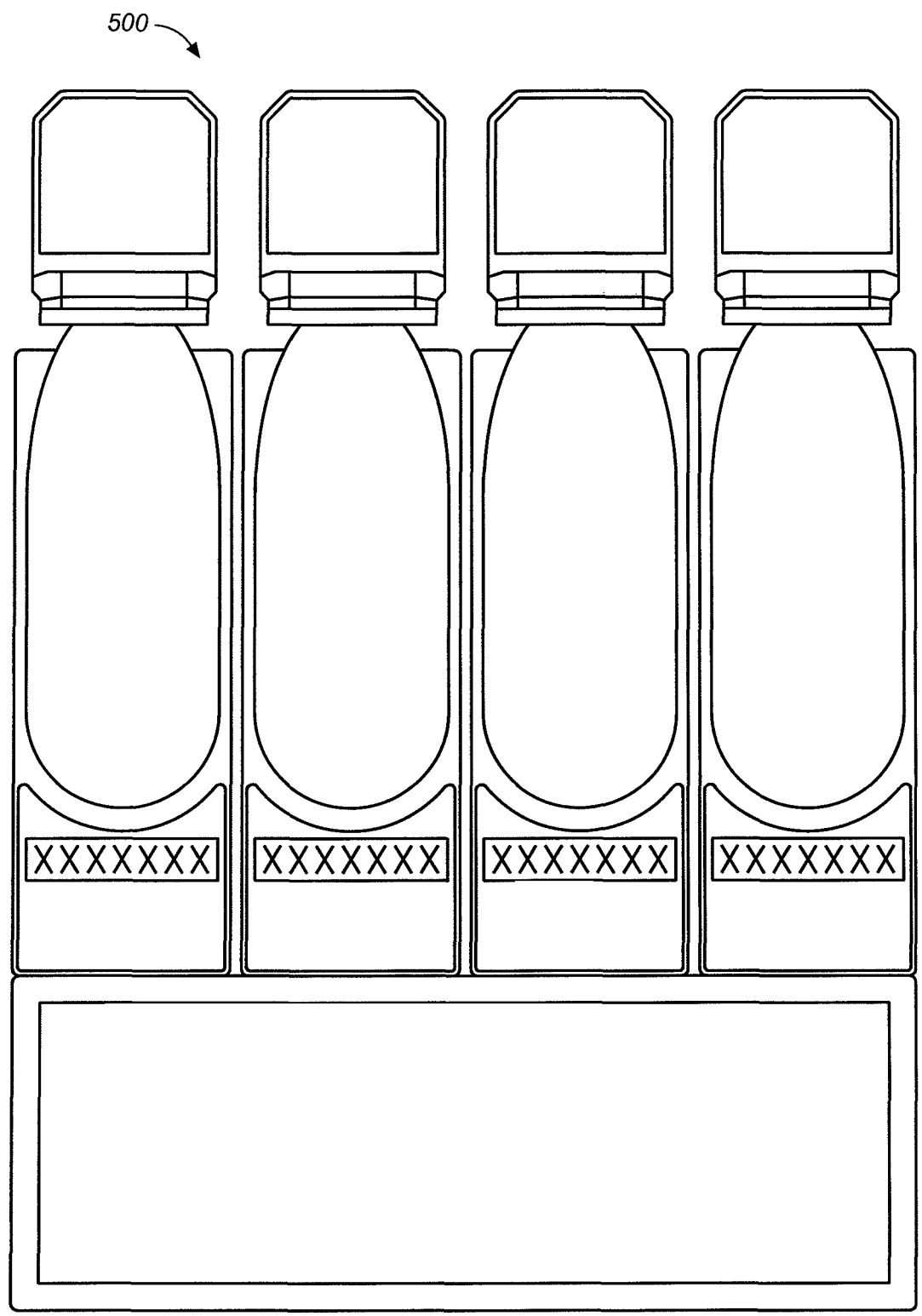
Figure 6:
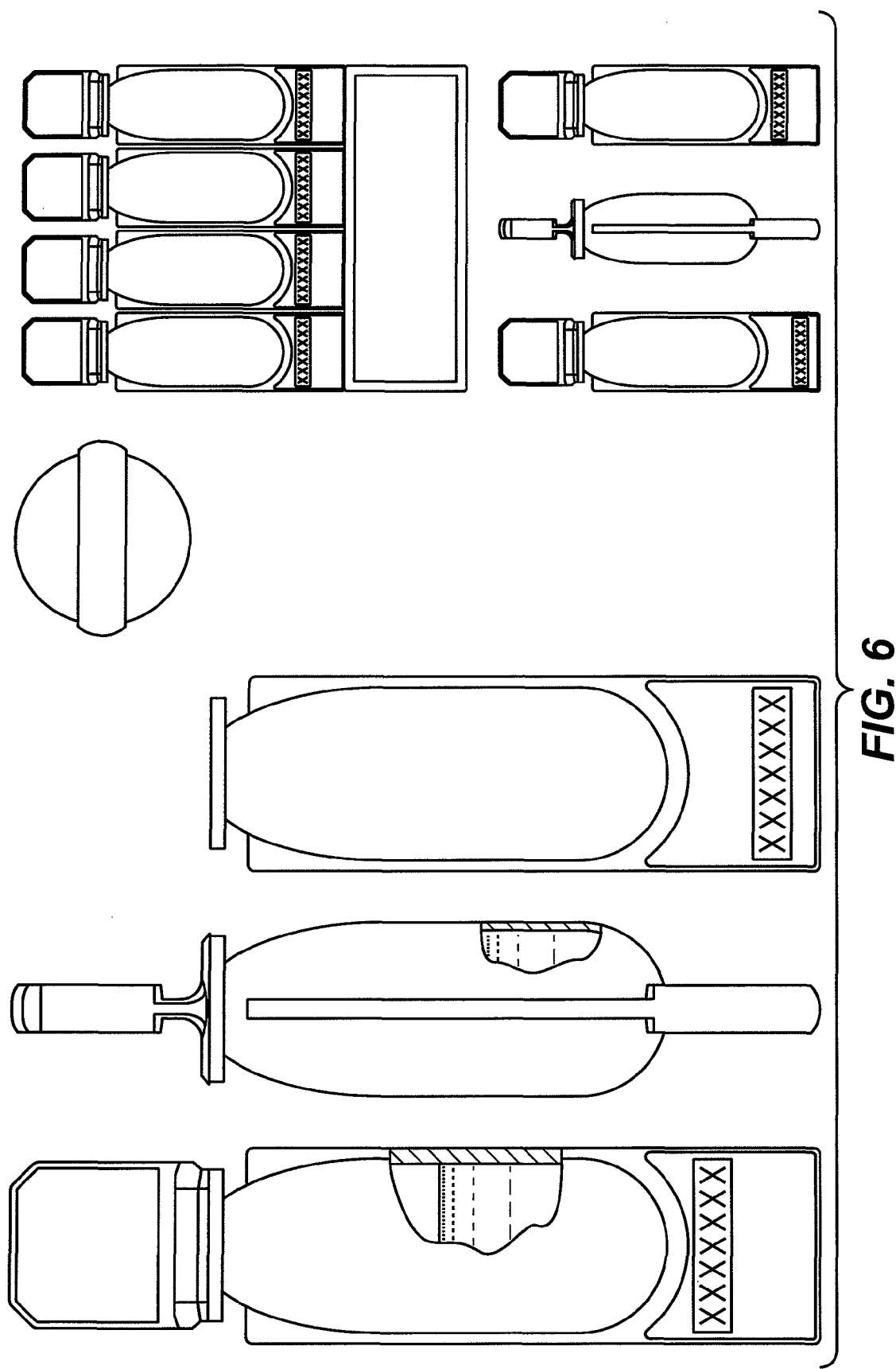

The containers are configured to hold less than about 2.0 ml of a formulation. In some variations, the containers are configured to hold 1.5 ml or less of a formulation. In other variations, the containers are designed to hold 1.0 ml or less of a formulation. In yet further variations, the containers are configured to hold about 0.5 ml of a formulation. In another variation, the containers are configured to hold about 50 μl of a formulation. The formulation may be of any form. For example, the formulation may contain the active agent in solution or suspension. Each container includes a unit dose amount of an active agent. The containers may be provided individually or as a sleeve of containers, as shown in FIG. 5. In some variations, the containers are provided as a sleeve of four containers. In other variations, the containers are provided as a sleeve of five or more containers.

Active Agents. Any active agent may be included in the containers described herein so long as they are suitable to treat systemic or local conditions, including, but not limited to, asthma or other pulmonary conditions, and the allergic or inflammatory conditions previously mentioned, and are capable of being formulated as a unit dose in a low volume for nebulization. The active agents may be particulate in form. The active agents may also be formulated as solutions, colloidal dispersions, inclusion complex solutions, foams, liposomal complexes, emulsions, or suspensions.

In one variation, the active agent is budesonide, a corticosteroid. Suitable budesonide formulations that may be used with the containers and methods described here include those disclosed in U.S. Pat. Nos. 6,264,922; 6,267,989; 6,811,767; 5,145,684; 5,346,702; U.S. application Ser. No. 11/409,922; U.S. application Ser. No. 11/654,600; U.S. application Ser. No. 10/264,030; U.S. application Ser. No. 11/275,775; and U.S. application Ser. No. 11/412,523, all of which are commonly owned and herein incorporated by reference in their entirety. Reference to budesonide includes, but is not limited to, any form of budesonide that may be used to treat asthma or COPD, including, but not limited to, derivatives, analogues, enantiomer forms, stereoisomers, anhydrides, acid addition salts, base salts, and solvates.

Other active agents that may be filled into the containers include, but are not limited to, anti-infective agents, anti-inflammatory agents, and chemotherapeutic agents. Anti-infective agents generally include antibacterial agents, antifungal agents, antiparasitic agents, and antiviral agents. Anti-inflammatory agents generally include steroidal and nonsteroidal anti-inflammatory agents.

Examples of antibacterial agents that may be suitable for use with the described methods and containers include, but are not limited to, aminoglycosides, amphenicols, ansamycins, β-lactams, lincosamides, macrolides, nitrofurans, quinolones, sulfonamides, sulfones, tetracyclines, vancomycin, and any of their derivatives, analogues, or combinations thereof.

Examples of antifungal agents suitable for use with the described methods and containers include, but are not limited to, allylamines, imidazoles, polyenes, thiocarbamates, triazoles, and any of their derivatives. In one variation, imidazoles are the preferred antifungal agents. Antiparasitic agents that may be employed include such agents as atovaquone, clindamycin, dapsone, iodoquinol, metronidazole, pentamidine, primaquine, pyrimethamine, sulfadiazine, trimethoprim/sulfamethoxazole, trimetrexate, and any of their derivatives, analogues, or combinations thereof.

Examples of antiviral agents suitable for use with the described methods and containers include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl) guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N-, N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and any of their derivatives, analogues, or combinations thereof.

Typically, a steroidal anti-inflammatory agent, e.g., a corticosteroid (glucocorticosteroid), is formulated for use with the containers and methods described herein. Exemplary steroidal anti-inflammatory agents include 21-acetoxypregnenolone, alclometasone, algestone, amcinonide, beclomethasone, betamethasone, chloroprednisone, ciclesonide, clobetasol, clobetasone, clocortolone, cloprednol, corticosterone, cortisone, cortivazol, deflazacort, desciclesonide, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, analogues, and combinations thereof.

If a nonsteroidal anti-inflammatory agent is used, suitable agents include, but are not limited to, COX inhibitors (COX-1 or COX nonspecific inhibitors) (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and selective COX-2 inhibitors (e.g., diaryl-substituted furanones such as rofecoxib; diaryl-substituted pyrazoles such as celecoxib; indole acetic acids such as etodolac and sulfonanilides such as nimesulide).

The chemotherapeutic/antineoplastic agents that may be used in the containers and methods described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin- 12 (IL-12), biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, analogues/congeners, derivatives of such compounds, and combinations thereof.

The formulations that may be filled into the containers described here may also include excipients and/or additives. Suitable formulations and excipients and/or additives that may be employed are found in U.S. Publication No. 2007/0178051, which is hereby incorporated by reference in its entirety. For example, the formulations may include one or more surface stabilizers (surface active agents), phospholipids, solubility enhancers, surface modifiers, antioxidants, chelating agents, or combinations thereof. Useful surface stabilizers include, but are not limited to, non-ionic surface stabilizers such as polyoxyethylene sorbitan esters and polysorbate 80. Useful phospholipids include without limitation, lecithin NF grades or synthetic phospholipids including lecithin NF, purified lecithin, hydrogenated lecithin, soy or egg lecithin phosphatides containing mixtures of anionic phosphatides such as phosphatidylinositol, phosphatidylserine, phosphatidic acid, phosphatidylglycerol, the corresponding lysophosphatides, synthetic phosphatidic acid, and mixtures thereof. Chelating agents include, but are not limited to, cyclodextrins, cromoglycates, xanthates including caffeine, pegylation agents, crown ethers, ethylenediaminetetraacetic acid (EDTA) or a salt thereof, such as the disodium salt, citric acid, nitrilotriacetic acid and the salts thereof. Antioxidants include, but are not limited to, vitamins, provitamins, ascorbic acid, vitamin E, or salts or esters thereof.

Other excipients that may be used, include, but are not limited to, one or more inclusion complexes, pH buffers, tonicity modifiers, binding agents, filling agents, lubricating agents, suspending agents, sweeteners, flavoring agents, preservatives, wetting agents, disintegrants, and effervescent agents.

Examples of suitable filling agents are lactose monohydrate, lactose anhydrous, and various starches. Examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (SMCC).

Suitable lubricants, including agents that act on the flowability of the powder to be compressed, are colloidal silicon dioxide, such as Aerosil® 200; talc, stearic acid, magnesium stearate, calcium stearate, and silica gel.

Examples of suitable sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of suitable preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of suitable diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

In some variations, the containers described here may contain a formulation that includes micronized budesonide, polysorbate 80, hydrogenated soy lecithin, and EDTA. For example, the formulation may comprise between about 0.0031% to about 0.025% by weight micronized budesonide, between about 0.0001% to about 1.0% by weight polysorbate 80, between about 0.00016% to about 0.00125% hydrogenated soy lecithin, and between about 0.0001% to about 5.0% by weight EDTA. In one variation, the formulation includes about 0.005% by weight EDTA. Exemplary low and high dose budesonide formulations are shown in Table 1. These formulations may be made by the process described in Example 1.

TABLE 1

Exemplary Budesonide Formulations

| Component | Content Per Unit Dose (Low Dose) | Content Per Unit Dose (High Dose) |
| --- | --- | --- |
| Budesonide, Micronized | 0.135 mg | 0.250 mg |
| Polysorbate 80 | 0.037 mg | 0.043 mg |
| Hydrogenated Soy Lecithin (S75-3) | 0.007 mg | 0.013 mg |
| EDTA (Edetate Disodium Dihydrate) | 0.075 mg | 0.075 mg |
| Sodium Chloride | 12.75 mg | 12.75 mg |
| Sodium Citrate Dihydrate | 0.94 mg | 0.94 mg |
| Citric Acid | 0.28 mg | 0.28 mg |
| Water for Injection | q.s. to 1.5 ml | q.s. to 1.5 ml |

Materials. The containers may be made from any suitable material that does not react with the formulation, and which does not allow substantial permeation of oxygen through the container wall. Glass may be used, but in some variations, a polymer is used. For example, thermoplastic polymers such as polycarbonate, polyethylene, including low density polyethylene (LDPE), polyester, polystyrene, polypropylene, polysulfone, polyurethane, ethylene-vinyl-acetate, and the like, may be used. The materials may be transparent, translucent, or colored. In some variations, Rexene® LDPE 1105 is the polymer used. In other variations, different materials may be employed to make different parts of the containers. For example, the cap, body, and identifier portions of the container may be made from different polymers.

The containers described here are configured to provide enhanced storage stability of the formulations contained therein, as further detailed in Examples 2 and 4-6. Examples 2, 4, and 5 show that there is substantially no surface adsorption of budesonide when the formulations are stored in the containers. Specifically, Example 2 shows that lowered wetted (internal) surface area increases drug recovery, even after prolonged storage. In Example 4, the decreased overage required to attain target strength of the formulation also demonstrates that surface adsorption has been minimized. In Example 4, it is shown that an overage of 0.12 mg/ml was required to attain target strength. This overage amount correlates to a budesonide surface adsorption value of 13%. Further support is found in the data provided in Example 6, where it is demonstrated that budesonide particle sizes did not substantially increase when the formulations were stored in the containers for prolonged periods. When stored for up to 18 months, the particles in the low concentration (0.135 mg/1.5 ml) budesonide formulation did not increase more than 150 nm in size. Particles sizes in the high concentration budesonide formulation (0.250 mg/1.5 ml) also did not increase more than 150 nm when stored for up to 12 months. Larger particles sizes after prolonged storage may be seen (e.g., particles in the high concentration budesonide formulation at 18 months) that are not statistically significant. Thus, particles sizes overall did not increase due to sedimentation and/or agglomeration. Although enhanced storage stability is demonstrated with the budesonide formulation described in Example 1, it is understood that the container and formulation combinations are not so limited, and that other formulations, including other corticosteroid formulations may be used with the containers described herein.

The containers also have lower residual volumes than conventional nebulizer ampules. As shown in Example 7, conventional vials (Pulmicort Respules®) were found to retain five times more volume than the containers described herein after one squeeze. For example, at a budesonide concentration of 0.135 mg/1.5 ml, volume retention was 6% of the fill volume, and at a budesonide concentration of 0.250 mg/1.5 ml, volume retention was 2.7% of the fill volume. In comparison, volume retention of the Pulmicort ampule after one squeeze was 32.9% of the fill volume. The lower retention volume after a single squeeze may be due to such factors as the size, shape, internal contour, or other design aspect of the containers (e.g., absence of a neck region).

II. METHODS

Delivery and Treatment. Methods for treating asthma and other pulmonary conditions are described. In general, the method involves providing a formulation containing an active agent for treating the pulmonary condition in one or more unit dose containers and administering the formulation via nebulization. The unit dose containers may be stored in a foil pouch to protect the active agents from being exposed to light. Typically, the foil pouch is opened by tearing along a serrated edge. One container is removed for immediate use, and the other unused containers, if any, are kept in the foil pouch. To open the container, the cap is twisted approximately 180° while holding the body of the container stable. A unit dose is then dispensed from the container by pouring or squeezing its contents into the nebulizer. The dose of the active agent administered may be from about 0.05 mg to about 10 mg. In some variations, the dose of the active agent administered ranges from about 0.05 mg to about 0.25 mg.

The volume of formulation within the unit dose container is less than about 2.0 ml. In some variations, the volume of the formulation within the unit dose container is about 1.5 ml or less, about 1.0 ml or less, about 0.5 ml or less, or as low as 0.15 ml. The low volume of formulation within the container results in a shorter delivery time for the unit dose of active agent. The active agent may be delivered to any structure or tissue within the respiratory system. For example, the active agent may be delivered to the larynx, trachea, bronchi, bronchioles, alveoli, or any combination thereof. In one variation, budesonide is provided in a unit dose container as herein described for nebulization to the respiratory system. Methods for treating allergic and inflammatory conditions involve the same or similar steps as those described above.

Methods For Making the Containers. The containers may be produced by such methods as injection molding or blow-fill-seal (BFS) processes, which are well known in the art. In one variation, the formulations are placed within the containers using BFS processes. The BFS process typically forms the container from an extruded polymer parison that is filled and sealed in a single aseptic operation. In a typical operation, to form the container, a thermoplastic polymer such as low density polyethylene, is continuously extruded in a tubular shape. When the tube reaches the proper length, the mold closes and the parison is cut. The bottom of the parison is pinched, closed and the top is held in place with a set of holding jaws. The mold is then transferred to a position under the filling station. To fill the container, the nozzle assembly lowers into the parison until the nozzles form a seal with the neck of the mold. Container formation is completed by applying vacuum on the mold side of the container and by blowing sterile filtered air into the interior of the container. The fill system delivers a precise dosage of product into the container. The nozzles then retract into their original position. Lastly, separate seal molds close to form the top and hermetically seal the container. The molds open and the container is then conveyed out of the machine. BFS machines are commercially available from a number of suppliers, including Weiler Engineering, Inc. (Elgin, Ill.) and Rommelag USA Inc. (Evergreen, Colo.). As previously mentioned, the containers may be produced as a series of sleeved containers.

III. KITS

The containers described here may be included in kits for delivering active agents to the respiratory system. The kits may include a plurality of single unit doses for use with a nebulizer, which in some instances provide treatment for about one week, and in other instances, about one month, or more. The kit may also include the unit dose containers provided in a sleeve. Furthermore, the kit may comprise individual unit dose containers or sleeves in which each container or sleeve includes a different active agent from another container or sleeve.

The kit may also include instructions as to how the unit dose container should be used with a nebulizer, such as how to open it and transfer its contents into the nebulizer, how to operate the nebulizer and for how long nebulizing should be continued to complete administration of the unit dose. The kit may also include instructions on how to mix the formulation (e.g., re-suspend or re-disperse particles of the active agent). In some variations, the re-dispersing step includes holding the container upright between the thumb and index finger, and then turning the container upside down and then back again to the upright position (inverting). The number of container inversions that are instructed may vary. In some instances, the instructions may require at least nine inversions of the container. In other variations, the re-dispersing step includes shaking the containers with a side-to-side wrist movement. The shaking may be slow-paced (approximately one shaking action per second), medium-paced (approximately three shaking actions per second), or fast-paced (approximately five shaking actions per second). The duration of shaking may also vary. For example, the instructions may require container shaking for about one second, for about three seconds, for about five seconds, or for about ten seconds.

IV. EXAMPLES

Example 1

Preparation of Budesonide Formulation

To form a unit dose budesonide formulation, budesonide particles are initially processed to produce a sterile bulk drug intermediate dispersion, which is further processed into a final aerosol formulation. In the initial processing, the crystalline budesonide starting material is subjected to a milling step to reduce the size of the budesonide particles. The milling step is accomplished by milling crystalline budesonide starting material in a dilute solution of polysorbate 80 (Tween 80) and a milling media to a substantially smaller diameter. The budesonide particles produced are stabilized by the subsequent addition of hydrogenated soy lecithin and disodium edetate. The resulting concentrated bulk drug intermediate dispersion is then sterilized. The bulk drug intermediate dispersion is further processed into a desired aerosol formulation by diluting it aseptically to the appropriate strength by addition of a sterile citrate-buffered isotonic saline solution. The final pH of the aerosol formulation may be from about pH 4 to about pH 7. It is understood that the amount of sodium citrate or citric acid added for dilution may be modified to produce the desired pH. The diluted dispersion is filled into the containers by the blow-fill-seal process previously described.

Example 2

Effect of Lowered Wetted (Internal) Surface Area on Drug Recovery

To be suitable for commercial and clinical supplies, an active agent product must maintain potency within 90% of label claim over its specified shelf life. To test formulation stability in a container having lowered wetted (internal) surface area, a low dose (approximately 0.135 mg/1.5 ml) and a high dose (approximately 0.25 mg/1.5 ml) of a drug formulation, such as described in Example 1 was examined. The experimental container was designed to hold about 1.5 to about 1.6 ml of aqueous active agent. A conventional 2.0 ml unit dose container having a wetted surface area of 3.06 square inches (19.7 square centimeters) and the experimental 1.65 ml unit dose container having a surface area of 1.50 square inches (9.68 square centimeters) were filled with 2.0 and 1.5 ml of the aqueous active agent suspension, respectively. A commercial comparator (Pulmicort Respules® ampule), which contained approximately the same active agent suspension with the same excipients, at the same strengths, was used as a reference.

After filling, the unit dose containers and the commercial reference were stored for six months at room temperature. At the time of filling and at six months, the decanted product (with or without shaking) was assayed for active agent content to determine available active agent potency. As shown in Table 2, the conventional container lost more than 30% potency, falling out of usable specifications, while the experimental design remained within 10% of original assay, and remained in specification. The commercial reference was used as a comparison and remained in specification only when shaken.

TABLE 2

Drug Recovered from Unit Dose Containers after Six Month Stability Aging at Room Temperature

| | Wetted Surface | | % Drug Recovery | |
| --- | --- | --- | --- | --- |
| | Area (in$^2$) | Volume (ml) | Low Dose | High Dose |
| Shaken | | | | |
| Conventional Container | 3.06 | 2.15 | 82 | 81 |
| Design of Invention | 1.50 | 1.65 | 95 | 93 |
| Pulmicort Respules ® | 3.12 | 2.12 | 87 | 84 |
| Not Shaken | | | | |
| Conventional Container | 3.06 | 2.15 | 72 | 92 |
| Design of Invention | 1.50 | 1.65 | 96 | 94 |
| Pulmicort Respules ® | 3.12 | 2.12 | 97 | 91 |

Example 3

Comparison of Nebulization Times

Figure 7:
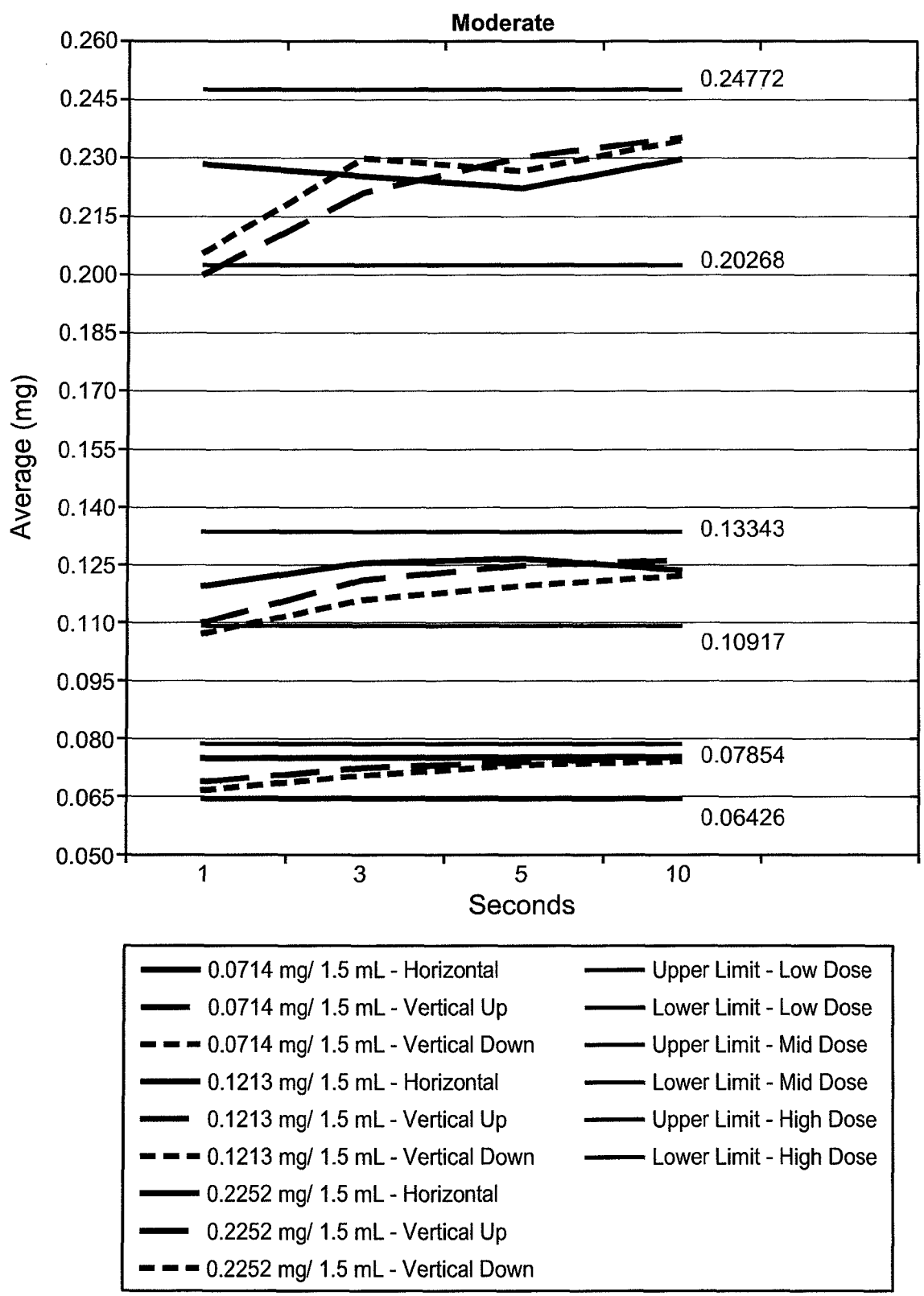
Figure 8:
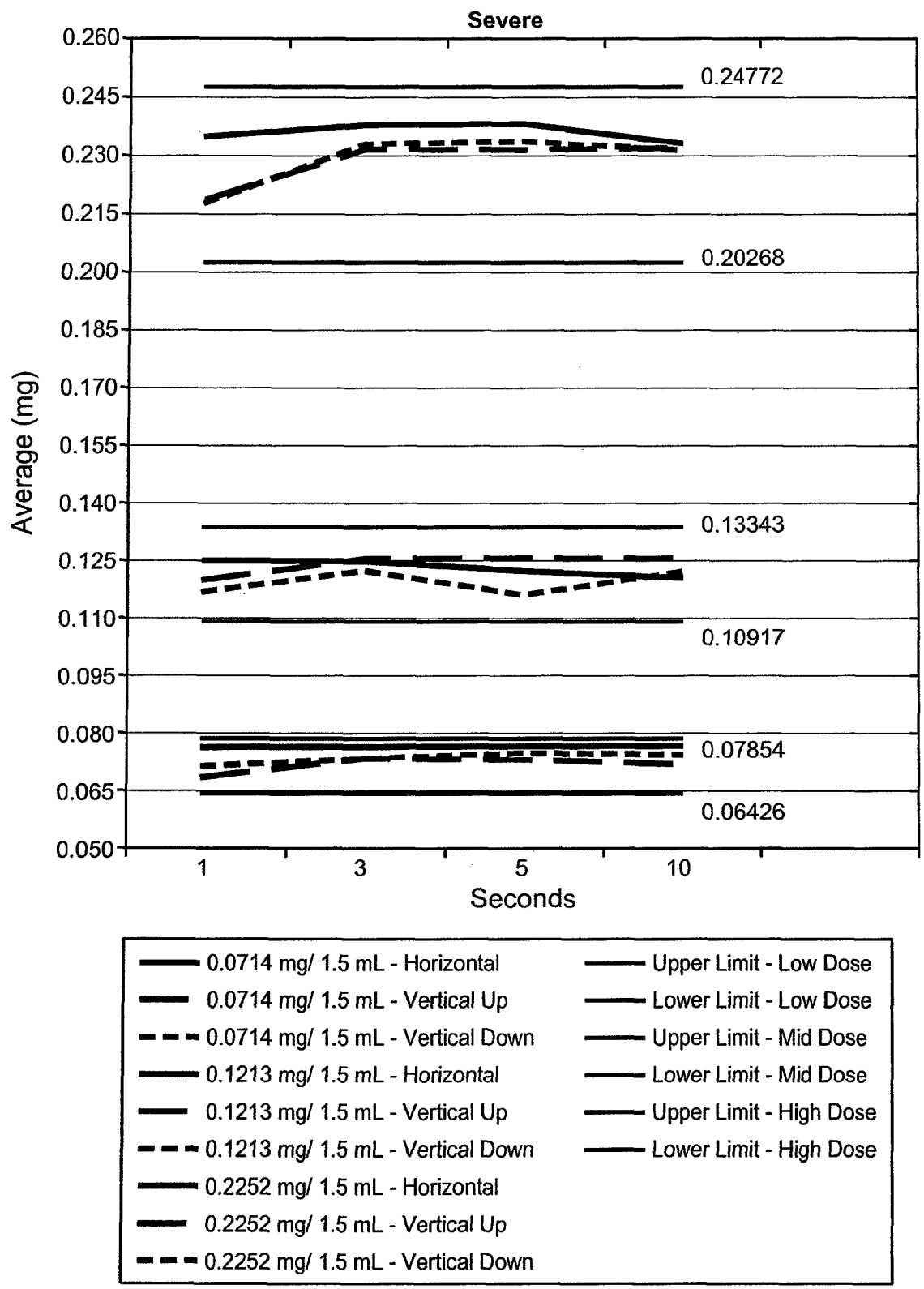

The same unit dose containers from Example 2 were administered to human subjects using a Pari LC nebulizer in conjunction with the ProNeb compressor (PARI). The time to sputtering, indicating completion of nebulization was monitored by clinical administrators. As shown in the Table 3, the unit dose of the design invention nebulized significantly faster than that for either the conventional unit dose container or the Pulmicort Respules. Further experiments resulted in a time to sputtering for conventional unit dose containers of six to eight minutes.

TABLE 3

Comparison of Nebulization Times

| | Volume (ml) | Time to Sputtering (mins) |
|---|---|---|
| Conventional Unit Dose Container | 2 | 8-9 |
| Design of Invention | 1.5 | 3-5 |
| Pulmicort Respules ® | 2 | 8-10 |

Example 4

Effect of Smooth Spherical Geometry in Minimizing the Amount of Retained Active Agent When conventional containers, as described in Example 2, were filled with bulk drug suspension, 0.025 mg/ml of active agent overage needed to be added to attain target strength. For the experimental containers, which were smoother and more spherical, as herein described, that overage was reduced to a 0.12 mg/ml overage to attain target strength. This overage amount correlates to 0.17 mg (13%) of the active agent adsorbing to the internal walls of the experimental containers.

Example 5

Container Effects on Surface Adsorption

In addition to maintenance of potency, shelf stability of the formulation made in Example 1 may be determined by assessing the amount of active agent adsorption to the internal surface of its container. To assay surface adsorption, the degree of re-suspension of particulate budesonide (% label claim) was examined after shaking containers using side-to-side wrist movements that had been stored for three weeks in horizontal, cap side up (vertical up), and cap side down (vertical down) orientations. Containers with measured concentrations of 0.0714 mg/1.5 ml (low dose), 0.1213 mg/ml (mid dose), and 0.2252 mg/ml (high dose) were tested. The containers were either moderately shaken (approximately three shaking actions per second) or severely shaken (approximately five shaking actions per second). The contents of the containers were then emptied and assayed for the amount of re-suspended active agent using the Agilent 1100 Series HPLC system (Santa Clara, Calif.). A total of six replicates for each dose were averaged and those values plotted versus duration in seconds from 1-10 for moderate and severe shaking across all three orientations. FIG. 7 depicts the graphical results for moderate shaking. FIG. 8 depicts the graphical results for severe shaking. The results show that severe and moderate shaking of the containers are sufficient to re-suspend/re-disperse the particulate budesonide across all label claim doses and orientations. In both FIGS. 7 and 8, the lower and upper limits of each dose (±10% of label claim) are indicated. Given that the lower limit is not exceeded for any label claim dose or orientation, not more than 10% of the particulate active agent is lost to surface adsorption.

Example 6

Container Effects on Formulation Stability

Shelf stability of the formulation described in Example 1 was also tested by analyzing particle size of the budesonide stored within the containers made according to the technique described in Example 2. The containers were stored in a horizontal orientation at 25° C. and 40% relative humidity (RH). Particle sizes were measured by static light scattering using a Horiba particle size analyzer (Irvine, Calif.). Tables 4 and 5 show that no significant change in particle size was observed over the extended storage period. If agglomeration had occurred, one skilled in the art would have expected to see significant size increases up to doubling or tripling of the initial particle size. Based on particles sizes, Table 4 shows no substantial agglomeration of particles in a budesonide formulation having a concentration of 0.135 mg/1.5 ml over a storage period of up to 12 months. Table 5 also shows no substantial agglomeration of particles in a budesonide formulation having a concentration of 0.250 mg/1.5 ml over a storage period of up to 12 months. This indicates that the container did not enable sedimentation which results in particle agglomeration.

TABLE 4

Budesonide Particle Size Over An 18 Month Storage Period (0.135 mg/1.5 ml)

| Test | Specification | Storage Time (months unless otherwise specified) | | | | | | |
|---|---|---|---|---|---|---|---|---|
| | | 0 | 6 Weeks | 3 | 6 | 9 | 12 | 18 |
| $D_{mean}=$ | NMT 600 nm | 417 nm | 444 nm | 425 nm | 450 nm | 446 nm | 525 nm | 447 nm |
| | | 410 nm | 444 nm | 420 nm | 453 nm | 445 nm | 520 nm | 446 nm |
| | | 411 nm | 446 nm | 424 nm | 455 nm | 444 nm | 521 nm | 446 nm |

TABLE 5

Budesonide Particle Size Over An 18 Month Storage Period (0.250 mg/1.5 ml)

| Test | Specification | Storage Time (months unless otherwise specified) | | | | | | |
|---|---|---|---|---|---|---|---|---|
| | | 0 | 6 Weeks | 3 | 6 | 9 | 12 | 18 |
| $D_{mean}=$ | NMT 600 nm | 410 nm | 439 nm | 442 nm | 450 nm | 451 nm | 438 nm | 1027 nm |
| | | 406 nm | 439 nm | 432 nm | 452 nm | 454 nm | 437 nm | 670 nm |
| | | 406 nm | 444 nm | 436 nm | 454 nm | 454 nm | 436 nm | 1051 nm |

Example 7

Comparison of Retention Volumes

In order to measure volume retention of the containers in comparison to that of Pulmicort Respules® ampules, each container or ampule was initially weighed. The contents of each were then dispensed into a beaker by inversion and squeezing the container or ampule once. The container or ampule was weighed again and the final weight recorded. The volume dispensed was also weighed. These steps were repeated three times for budesonide concentrations of 0.135 mg/1.5 ml and 0.250 mg/1.5 ml for the containers, and three times for the budesonide concentration of 0.250 mg/2.0 ml for the Pulmicort ampule. To determine the residual volume (ml), the sum of the weights of dispensed volume and the final weight was subtracted from the initial weight and divided by 1.005 (density of the fluid), which were 1.65 ml for the containers and 2.17 ml for the Pulmicort ampule. Data from the three trials is provided in Table 6.

TABLE 6

Residual Volumes (% of Fill Volume)

| | Containers (n = 3) | | Pulmicort (n = 3) |
|---|---|---|---|
| | 0.135 mg/ 1.5 mL | 0.25 mg/ 1.5 mL | 0.25 mg/ 2.0 mL |
| Mean | 6.021 | 2.697 | 32.884 |
| SD | 2.763 | 1.143 | 1.415 |

The invention claimed is:

1. A unit dose container for inhalation therapy comprising:
   (a) a body having a cavity containing a liquid formulation therein, the cavity having a cavity wall and a wetted surface area of about 9.7 square centimeters or less; and
   (b) a dispensing end in fluid communication with the cavity, wherein the convergence between the cavity and the dispensing end is smooth and continuous and wherein the dispensing end does not form a neck region with the body,
   wherein the formulation comprises particles of an active agent.

2. The unit dose container of claim 1 wherein less than 20% of the active agent is adsorbed to the cavity wall.

3. The unit dose container of claim 1 wherein less than 15% of the active agent is adsorbed to the cavity wall.

4. The unit dose container of claim 1, further comprising a frangible cap attached to the dispensing end.

5. The unit dose container of claim 1, wherein the dispensing end has a diameter between about 0.5 cm to about 1.5 cm.

6. The unit dose container of claim 1, wherein the cavity is configured to hold between about 50 µl to about 2.0 ml of the formulation.

7. The unit dose container of claim 6, wherein the cavity is configured to hold about 0.5 ml to about 1.6 ml of the formulation.

8. The unit dose container of claim 7, wherein the cavity is configured to hold about 1.6 ml of the formulation.

9. The unit dose container of claim 1, wherein the active agent is selected from the group consisting of anti-infective agents, anti-inflammatory agents, chemotherapeutic agents, and combinations thereof.

10. The unit dose container of claim 9, wherein the active agent comprises an anti-inflammatory agent.

11. The unit dose container of claim 10, wherein the anti-inflammatory agent comprises a corticosteroid.

12. The unit dose container of claim 11, wherein the corticosteroid comprises budesonide or a derivative or analogue thereof.

13. The unit dose container of claim 12, wherein not more than about 0.17 mg of budesonide is adsorbed to the cavity wall.

14. The unit dose container of claim 1, wherein the wetted surface area is less than about 6.44 square centimeters.

15. The unit dose container of claim 1, wherein the wetted surface area is less than about 3.22 square centimeters.

16. The unit dose container of claim 1, wherein the wetted surface area is less than about 1.61 square centimeters.

17. The unit dose container of claim 1 comprising a polymer selected from the group consisting of polycarbonate, polyethylene, low density polyethylene (LDPE), polyester, polystyrene, polypropylene, polysulfone, polyurethane, ethylene-vinyl-acetate, and combinations thereof.

18. The unit dose container of claim 17, wherein the polymer comprises LDPE.

19. The unit dose container of claim 1, wherein the formulation has a concentration of 0.135 mg per 1.5 ml of active agent, and the formulation is stored for up to 12 months at 25° C. and 40% relative humidity with no substantial agglomeration of the active agent particles.

20. The unit dose container of claim 19, wherein the active agent particles have an average particle size of between about 400 nm to about 550 nm.

21. The unit dose container of claim 1, wherein the formulation has a concentration of 0.250 mg per 1.5 ml, and the formulation is stored for up to 12 months at 25° C. and 40% relative humidity with no substantial agglomeration of the active agent particles.

22. The unit dose container of claim 21, wherein the active agent particles have an average particle size of between about 400 nm to about 550 nm.

23. The unit dose container of claim 1, wherein the formulation further comprises a surface active agent, a phospholipid, EDTA, or a combination thereof.

24. The unit dose container of claim 12, wherein the formulation further comprises a surface active agent, a phospholipid, EDTA., or a combination thereof.

25. The unit dose container of claim 1, wherein the container has a retention volume of less than about 6% of the fill volume.

26. The unit dose container of claim 1, wherein the container has a retention volume of less than about 3% of the fill volume.

* * * * *

UNITED STATES PATENT AND TRADEMARK OFFICE
CERTIFICATE OF CORRECTION

| | | |
|---|---|---|
| PATENT NO. | : 8,486,043 B2 | Page 1 of 1 |
| APPLICATION NO. | : 12/250516 | |
| DATED | : July 16, 2013 | |
| INVENTOR(S) | : Laxmi Iyer et al. | |

It is certified that error appears in the above-identified patent and that said Letters Patent is hereby corrected as shown below:

On the Title page, in item (56), under "OTHER PUBLICATIONS", in column 2, line 2, after "application" insert -- No. --.

In the Specifications:

In column 1, line 56, after "Ingelheim" delete "Ingelheim".

In column 6, line 24, delete "the" and insert -- The --, therefor.

In column 7, line 42, delete "formivirsen" and insert -- fomivirsen --, therefor.

In column 8, line 23, delete "dicofenac" and insert -- diclofenac --, therefor.

In column 8, line 55, delete "ingibitors" and insert -- inhibitors --, therefor.

In column 8, line 56, delete "trriazole" and insert -- triazole --, therefor.

In column 9, line 5, delete "cchlorambucil" and insert -- chlorambucil --, therefor.

In column 9, line 10, delete "mitoazitrone" and insert -- mitoxantrone --, therefor.

In column 9, line 49, delete "silicifized" and insert -- silicified --, therefor.

In column 9, line 56, delete "acsulfame" and insert -- acesulfame --, therefor.

In the Claims:

In column 18, line 35, in claim 24, delete "EDTA.," and insert -- EDTA, --, therefor.

Signed and Sealed this
Eighteenth Day of March, 2014

Michelle K. Lee
*Deputy Director of the United States Patent and Trademark Office*